(12) United States Patent
Evans et al.

(10) Patent No.: US 8,734,331 B2
(45) Date of Patent: May 27, 2014

(54) EXPANDABLE BLOOD PUMPS AND METHODS OF THEIR DEPLOYMENT AND USE

(75) Inventors: Don W. E. Evans, Saint Paul, MN (US); Jeremy John Maniak, Edina, MN (US)

(73) Assignee: Minnetronix, Inc., St. Paul, MN (US)

( * ) Notice: Subject to any disclaimer, the term of this patent is extended or adjusted under 35 U.S.C. 154(b) by 0 days.

(21) Appl. No.: 13/590,488

(22) Filed: Aug. 21, 2012

(65) Prior Publication Data
US 2013/0085319 A1   Apr. 4, 2013

Related U.S. Application Data

(60) Provisional application No. 61/528,536, filed on Aug. 29, 2011.

(51) Int. Cl.
*A61B 1/00* (2006.01)

(52) U.S. Cl.
USPC ........................................................ 600/116

(58) Field of Classification Search
USPC ........................................................ 607/116
See application file for complete search history.

(56) References Cited

U.S. PATENT DOCUMENTS

| | | | |
|---|---|---|---|
| 4,105,016 A | 8/1978 | Donovan, Jr. | |
| 4,753,221 A | 6/1988 | Kensey et al. | |
| 6,533,716 B1 | 3/2003 | Schmitz-Rode et al. | |
| 6,827,682 B2 | 12/2004 | Bugge et al. | |
| 6,974,436 B1 | 12/2005 | Aboul-Hosn et al. | |
| 6,981,942 B2 | 1/2006 | Khaw et al. | |
| 7,027,875 B2 | 4/2006 | Siess et al. | |
| 7,070,555 B2 | 7/2006 | Siess | |
| 7,638,915 B2 | 12/2009 | Sentmanat | |
| 7,841,976 B2 | 11/2010 | McBride et al. | |
| 7,878,967 B1 | 2/2011 | Khanal | |
| 7,942,804 B2 | 5/2011 | Khaw | |
| 8,371,997 B2 | 2/2013 | Shifflette | |
| 2006/0245959 A1* | 11/2006 | LaRose et al. ............. 417/423.5 |
| 2008/0103591 A1 | 5/2008 | Siess | |

(Continued)

FOREIGN PATENT DOCUMENTS

| | | |
|---|---|---|
| EP | 2 229 965 | 9/2010 |
| EP | 2 338 541 | 6/2011 |

(Continued)

OTHER PUBLICATIONS

International Search Report and Written Opinion mailed on Dec. 7, 2012 in connection with International Patent Application No. PCT/US2012/052031. 13 pages.

(Continued)

*Primary Examiner* — Robert N Wieland
(74) *Attorney, Agent, or Firm* — Kenneth E. Levitt; Dorsey & Whitney

(57) ABSTRACT

A pump for inducing motion of a fluid, the pump including a cannula adjustable between an operable configuration having a first diameter and a deployment configuration having a substantially smaller second diameter. An impeller is rotatable within the cannula about an axis. The impeller includes an at least semi-rigid support for a flexible web, and is positionable with respect to the cannula the operable configuration and the deployment configuration, the operable configuration extending the web to a first radial distance from the axis and the deployment configuration collapsing the web to a second substantially smaller radial distance from the axis.

20 Claims, 12 Drawing Sheets

(56) References Cited

U.S. PATENT DOCUMENTS

| | | |
|---|---|---|
| 2008/0114339 A1 | 5/2008 | McBride et al. |
| 2008/0132747 A1 | 6/2008 | Shifflette |
| 2008/0132748 A1 | 6/2008 | Shifflette |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2010/0191035 A1 | 7/2010 | Kang et al. |
| 2011/0009687 A1 | 1/2011 | Mohl |
| 2011/0071338 A1 | 3/2011 | McBride et al. |
| 2011/0106120 A1 | 5/2011 | Haselby et al. |
| 2013/0066140 A1* | 3/2013 | McBride et al. ............ 600/16 |

FOREIGN PATENT DOCUMENTS

| | | |
|---|---|---|
| WO | WO 03/103745 | 12/2003 |
| WO | WO 2010/042546 | 4/2010 |
| WO | WO 2010/105854 | 9/2010 |
| WO | WO 2011/035926 | 3/2011 |
| WO | WO 2011/089022 | 7/2011 |

OTHER PUBLICATIONS

International Search Report and Written Opinion mailed on Dec. 12, 2012 in connection with International Patent Application No. PCT/US2012/052034. 14 pages.

* cited by examiner

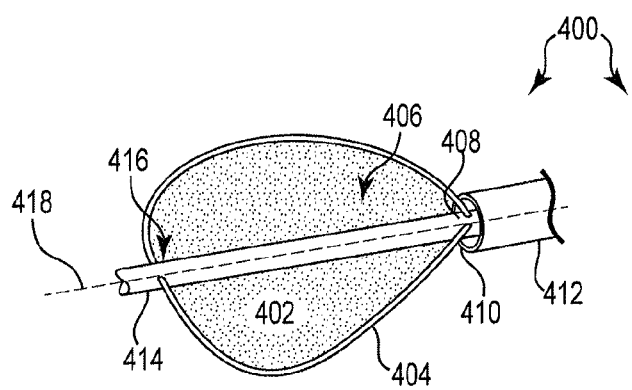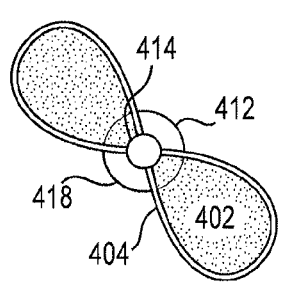
Fig. 4A  Fig. 4B
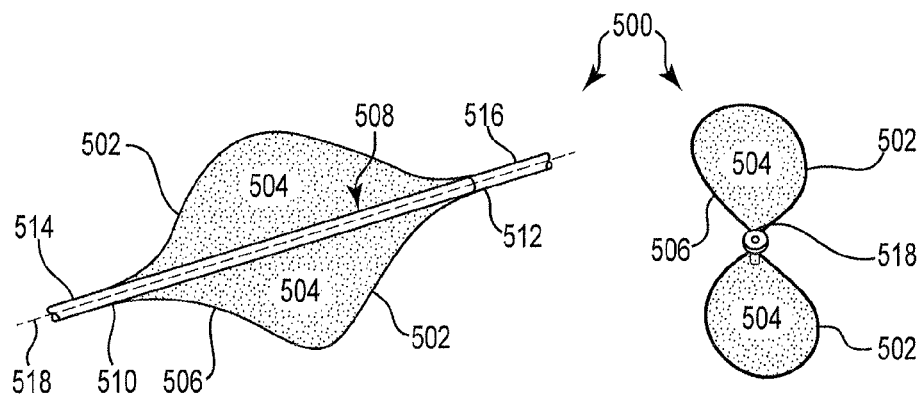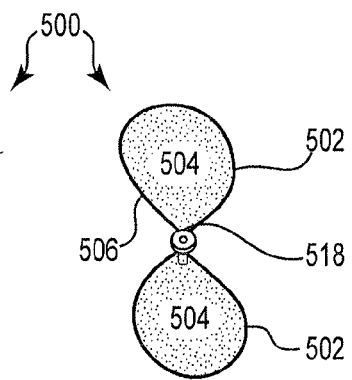
Fig. 5A  Fig. 5B

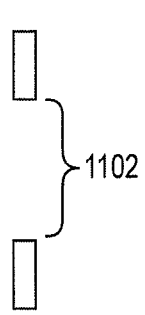 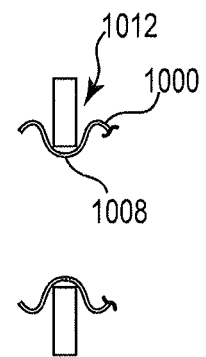
Fig. 11A       Fig. 11B
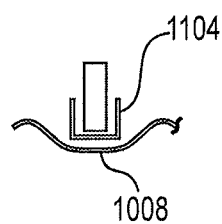
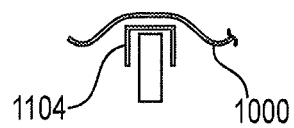
Fig. 11C

EXPANDABLE BLOOD PUMPS AND METHODS OF THEIR DEPLOYMENT AND USE

CROSS-REFERENCE TO RELATED APPLICATIONS

This application claims priority to U.S. Provisional Application No. 61/528,536 filed Aug. 29, 2011, the entirety of which is incorporated by reference herein. This application is related to co-pending U.S. application Ser. No. 13/590,564 to Evans et al., entitled EXPANDABLE VASCULAR PUMP and filed on Aug. 21, 2012, the entirety of which is incorporated by reference herein.

FIELD OF THE INVENTION

The present disclosure relates to blood pumps for acute cardiac support. More particularly, the present disclosure relates to expandable blood pumps and methods of their deployment and use for quickly providing temporary circulatory support.

BACKGROUND

A variety of cardiac problems result in the need for temporary cardiac support. These scenarios can range from contingency support during high risk cardiac surgery to immediate full support after a myocardial infarction. Acute pumps for temporary cardiac support differ from implantable pumps because the period of use may be measured short-term, in days or weeks, rather than long-term months or years. These situations requiring temporary cardiac support can benefit strongly from quick deployment in a range of anatomical locations.

Thus, there exists a need in the art for blood pumps that can improve aspects of this type of therapy. Particularly, there is a need in the art for improved expandable blood pumps for acute cardiac support.

SUMMARY

The present disclosure, in one embodiment, relates to expandable blood pumps and methods of their deployment and use for quickly providing temporary circulatory support. The blood pump may include a cannula constructed of an adjustable support member and flexible mesh cover allowing a deployment configuration of reduced or minimum collapsed size and an operable configuration of increased or maximum expanded size. In one embodiment, the cannula may vary in diameter along its axial length reducing or minimizing the interference between the expanded cannula and tissue openings. In addition, cannula diameter variation can allow for a leading narrow portion of the cannula which can improve maneuverability and permit an increased reach in anatomy. Further yet, cannula diameter variation can allow means for fixing the position of the pump with respect to a vessel opening or other port that it passes through. The cannula may include multiple openings, which can assist in preventing zero flow if a tissue collapses at the inlet end of the cannula. The cannula, in some embodiments, may be configured such that an outlet ejects flow generally perpendicularly to the pump's axis of rotation. The blood pump may be powered by a fluid system including catheter supply and return channels that cause a mechanical generator to rotate. The mechanical generator may be mechanically or magnetically coupled to an impeller of the blood pump.

The present disclosure, in another embodiment, relates to a pump for inducing motion of a fluid relative the pump. The pump may include an elongated cannula having at least one section adjustable between an operable configuration having a first diameter and a deployment configuration having a substantially smaller diameter. The pump may also include an impeller positioned within the adjustable section of the cannula and rotatable therein about an impeller axis. The impeller can include a rigid or semi-rigid mast supporting a flexible web, the mast being separately positionable with respect to the cannula between an operable configuration and a deployment configuration, the operable configuration extending at least a portion of the web to a first radial distance from the impeller axis and the deployment configuration collapsing the portion of the web to a second radial position of substantially shorter distance from the impeller axis. In some embodiments, the cannula may include a spiral support member, the spiral support member spiraling about the impeller axis. The spiral support member may be adjustable from the operable configuration to the deployment configuration by twisting the spiral support member. Alternatively or additionally, the spiral support member may be adjustable from the operable configuration to the deployment configuration by axially positioning a proximal and distal end of the spiral support member further away from one another. The cannula may further include a cover supported by the spiral support member. The cover, in some instances, may comprise a plurality of inlet openings and/or an outlet opening permitting flow to exit the pump substantially perpendicularly to the impeller axis. In some embodiments, the cannula may also include a second section adjustable between an operable configuration having a second diameter and a deployment configuration having a diameter substantially smaller than the second diameter. In particular embodiments, the cannula can include a port fixation neck between the first and second cannula sections.

In further embodiments, the impeller may have two rigid or semi-rigid masts supporting the flexible web, the masts in the operable configuration being substantially perpendicular to the impeller axis and in the deployment configuration being substantially parallel to the impeller axis. A distal catheter section may support a first one of the masts and a proximal catheter section may support a second one of the masts, at least one of the distal and proximal catheter sections being rotatable with respect to the other so as to radially offset the two masts. In other embodiments, a first end of the rigid or semi-rigid mast may be operably connected with a first catheter section of the impeller and a second end of the rigid or semi-rigid mast may be operably connected with a second catheter section, at least one of the first and second catheter sections being axially positionable with respect to the other, such that as the catheter sections are positioned toward each other, the mast is forced toward the operable configuration and as the catheter sections are moved away from each other, the mast is forced toward the deployment configuration. Additionally, at least one of the first and second catheter sections may be rotatable with respect to the other so as to radially offset the first and second mast ends.

The pump may include a drive shaft for driving a rotating motion of the impeller. The drive shaft may include a proximal section having a first gear at its distal end and a distal section having a second gear at its proximal end, rotation of the proximal section being transferred to the distal section by adjacently positioning the first and second gears. In another embodiment, a power transmission system of the pump for driving a rotational motion of the impeller may include a mechanical generator for transferring fluid motion therethrough into rotational motion of the generator about the impeller axis and a first lumen driving fluid to the mechanical generator and a second lumen transferring fluid away from the mechanical generator. The mechanical generator may be operably connected with the impeller, thereby transferring rotational motion of the generator about the impeller axis to rotational motion of the impeller about the impeller axis. In a further embodiment, the power transmission system may further include one or more first magnets radially positioned about the impeller axis and operably connected at or near a distal end of the mechanical generator and rotatable therewith about the impeller axis and a magnet housing operably connected with the impeller and positioned adjacent the distal end of the mechanical generator, the housing having one or more second magnets radially positioned about the impeller axis interacting with the first magnets to magnetically transfer rotational motion of the first magnets to rotational motion of the second magnets about the impeller axis.

The present disclosure, in yet a further embodiment, relates to a method of deploying a pump for acute cardiac support. The method may generally include providing a pump, such as that described above, inserting a catheter with the pump operably connected at or near the distal end thereof into a blood vessel with the cannula and impeller in their deployment configurations, guiding the pump to a desired location, and adjusting the cannula and impeller from their deployment configurations to their operable configurations. The method may also include adjusting the rigid or semi-rigid mast and flexible web to create a desired impeller blade angle. The impeller may be driven at a desired speed via a power transmission system. The method may also include adjusting the cannula and impeller back to their deployment configurations and removing the catheter and pump from the blood vessel.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the embodiments will be better understood from the following description taken in conjunction with the accompanying Figures, in which:

FIG. 4A is a perspective view of an impeller according to another embodiment of the present disclosure.

FIG. 4B is an end view of the impeller of FIG. 4A.

FIG. 5A is a perspective view of an impeller according to yet another embodiment of the present disclosure.

FIG. 5B is an end view of the impeller of FIG. 5A.

FIG. 11A is a side schematic view of an opening in a wall between any combination of heart chamber(s) and blood vessel(s).

FIG. 11B is a side schematic view of the cannula embodiment of FIG. 10A fixed within the opening of FIG. 11A.

FIG. 11C is a side schematic view of the cannula embodiment of FIG. 10A fixed within the opening of FIG. 11A, wherein the opening also has an intermediate device fixed at the wall opening.

DETAILED DESCRIPTION

The present disclosure relates to novel and advantageous blood pumps for acute cardiac support. Particularly, the present disclosure relates to novel and advantageous expandable blood pumps and methods of their deployment and use for quickly providing temporary circulatory support. Example uses of the various embodiments of expandable blood pumps provided herein can range from contingency support during high risk cardiac surgery to immediate full support after a myocardial infarction.

In general, a pump, with a cannula and impeller in a collapsed, deployment configuration, may be inserted into, for example, a major blood vessel and guided to the heart. Once the pump is placed in or near the desired location, e.g., desired chamber of the heart, the clinician or operator may use catheter controls to expand the pump's cannula. With the cannula expanded and a conduit created, the clinician or operator may then expand the pump's impeller within the cannula. Rotation of the impeller generates blood flow within the cannula between the cannula's inlet and outlet. The cannula may also provide separation between any surrounding tissue and the rotating impeller. The impeller may be driven via a power transmission system in the catheter and controlled from a control and/or power unit. The clinician or operator may enter therapeutic system parameters into the control unit, which drives the pump at the desired speed. The collapsed, deployment configuration may permit quick insertion to, and removal from, several anatomical positions while the expanded, operable configuration may permit appropriate therapy.

Figure 1:
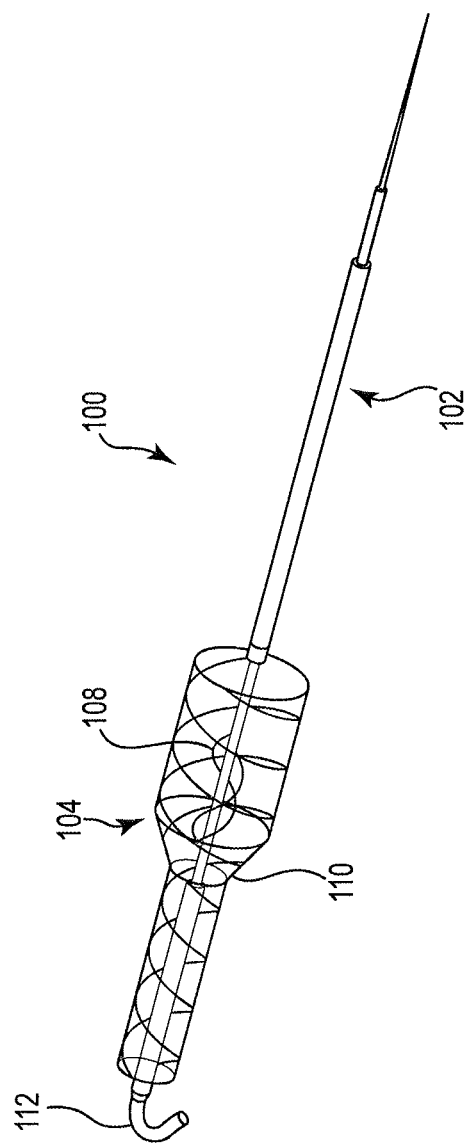
FIG. 1 is a perspective view of an expandable blood pump according to one embodiment of the present disclosure.
Figure 2:
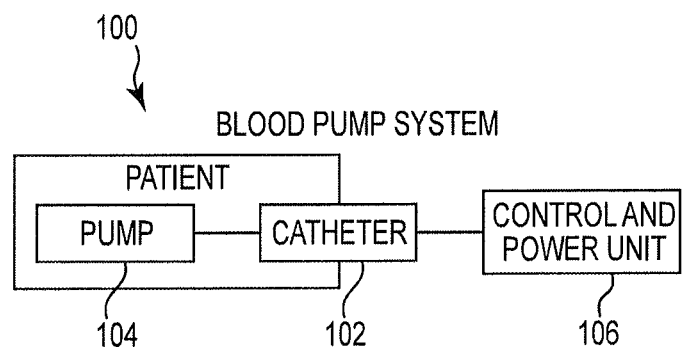
FIG. 2 is a schematic diagram of an expandable blood pump according to one embodiment of the present disclosure.

FIG. 1 illustrates one embodiment of an expandable blood pump 100 according to the present disclosure. With additional reference to FIG. 2, an expandable blood pump 100 may generally include a catheter 102 with a pump 104 positioned at or near the inserted end of the catheter and a control and/or drive unit 106 operably connected at or to an external end of the catheter. The pump 104 may include an impeller 108, a cannula 110, and a guidance system 112. The catheter 102 may include a power transmission system operably coupling the pump 104 and the control and/or drive unit 106. Several of these components, such as but not limited to, the impeller 108, cannula 110, guidance system 112, and power transmission system, can have various embodiments, which may be interchanged or interchangeable within the blood pump 100 to create a variety of different blood pump embodiments, which will be understood from the following description.

Impeller

In general, the various embodiments of impellers of the present disclosure may include one or more impeller blades comprising a thin, flexible web or film of material suspended by or between one or more generally moveable, rigid or semi-rigid support members or masts. In the various embodiments of impellers disclosed herein, the impeller may be activated between a collapsed, deployment configuration and an expanded, operable configuration by changing the position of the moveable, rigid or semi-rigid support members, thereby stretching the flexible web into a desired position and creating an impeller blade surface. That is, by virtue of the flexible web and moveable, rigid or semi-rigid support members, the impeller may permit a collapsed, deployment configuration of reduced or minimum size and an expanded, operable configuration of increased or maximum size. In some embodiments, the impeller may be activated between a collapsed, deployment configuration and an expanded, operable configuration separately from an activation of the cannula (discussed in further detail below) between a collapsed, deployment configuration and an expanded, operable configuration. In various embodiments disclosed herein, the impeller blades' geometries and scales can reduce hemolysis, thereby improving procedure outcomes due to improved therapy.

Figure 3:
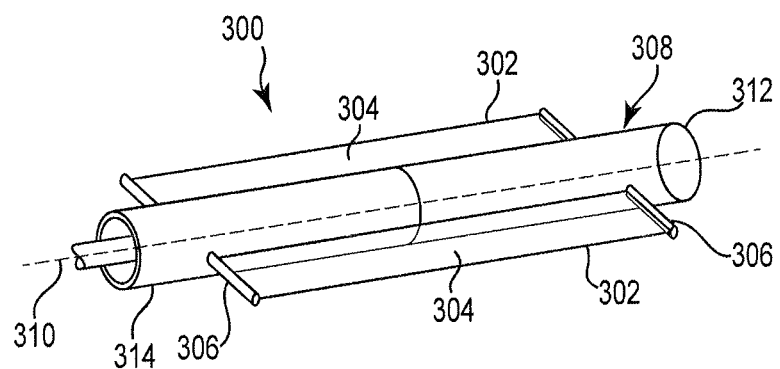
FIG. 3 is a perspective view of an impeller according to one embodiment of the present disclosure.

In one embodiment, illustrated in FIG. 3, an impeller 300 may be comprised of one or more impeller blades 302, each blade having a flexible web 304 suspended between rigid or semi-rigid, cantilevered support members 306 attached to the catheter 308. The support members 306 may be rotated or adjusted between positions substantially parallel and perpendicular to the pump's rotational axis 310. With the support members 306 in a position substantially parallel to the pump's rotational axis 310, the flexible web 304 may be retracted therewith to a collapsed, deployment configuration. As the support members 306 are adjusted to a position substantially perpendicular to the pump's rotational axis 310, as illustrated in FIG. 3, the flexible web 304 may be extended therewith to an expanded, operable configuration.

The catheter 308 may include a catheter layer having a proximal section 312 and a distal section 314, which may be rotated relative one another. Each blade 302 may have a support member 306 positioned at the proximal section 312 and a support member at the distal section 314. In this manner, with the flexible web 304 in an expanded, operable configuration, the angle of the flexible web, and thus the impeller blade surface, may be created or modified by rotation of the proximal 312 and distal 314 sections of the catheter 308 relative one another.

In another embodiment, illustrated in FIGS. 4A and 4B, an impeller 400 may include a flexible web 402 suspended by or between a generally semi-rigid, but flexible support member 404 and optionally the catheter 406. The generally semi-rigid, but flexible support member 404, in some embodiments, may be but is not limited to a moderate stiffness wire, and may be attached at both ends 408, 410 to the catheter 406. In one embodiment, the catheter 406 may include a sliding section 412 and a rotational section 414, which may be rotated relative to the sliding section, and the support member 404 may be attached at both ends 408, 410 to the sliding section of the catheter. A portion of the support member 404 may also be generally held in place axially at a fixed location 416 along the rotational section 414. For example, in one embodiment, the flexible support member 404 may pass through the rotational section 414, as shown in FIG. 4A, such that a portion of the support member is generally held in place axially at fixed location 416 along the rotational section. In another embodiment, the support member 404 may be split into two sections, each section having an end attached to the sliding section 412 and an end attached to the rotational section 414 at fixed location 416. However, other suitable means for permitting proximal and distal ends of the flexible support member 404 to move axially relative one another are considered within the spirit and scope of the present disclosure.

The sliding section 412 of the catheter 406 may be slid or axially adjusted along the rotational section 414 between axial positions toward and away from fixed location 416. With the sliding section 412 slid to a position generally relatively away from fixed location 416, portions of the support member 404 may be pulled closer to the pump's rotational axis 418, thereby causing the flexible web 402 to be retracted therewith to a collapsed, deployment configuration. As the sliding section 412 is slid to a position generally relatively toward the fixed location 416, portions of the support member 404 may be forced away from the pump's rotational axis 418, thereby causing the flexible web 402 to be expanded therewith to an expanded, operable configuration, as illustrated in FIG. 4A. With the flexible web 402 in an expanded, operable configuration, the angle of the flexible web, and thus the impeller blade surface, may be created or modified by rotation of the rotational section 414 of the catheter 406 with respect to the sliding section 412, as illustrated in FIG. 4B.

In yet another embodiment, illustrated in FIGS. 5A and 5B, an impeller 500 may include one or more impeller blades 502, which may each include a flexible web 504 suspended by or between a generally semi-rigid, but flexible support member 506 and optionally the catheter 508. The generally semi-rigid, but flexible support member 504, in some embodiments, may be but is not limited to a moderate stiffness wire, and may be attached at both ends 510, 512 to the catheter 508. In one embodiment, the catheter 508 may include a catheter layer having a distal section 514 and a proximal section 516, with either or both sections axially positionable along the pump's rotational axis 518 and either or both sections rotatable about the pump's rotational axis, such that the distal and proximal sections may be axially positioned and rotated relative to one another. The support member 506 may be attached at one end 510 to the distal section 514 and at one end 512 to the proximal section 516, thereby permitting the ends to also be axially positioned and rotated relative one another by means of the distal and proximal sections. However, other suitable means for permitting distal 510 and proximal 512 ends of the flexible support member 506 to move axially and/or rotationally relative one another are considered within the spirit and scope of the present disclosure.

Either or both of the distal 514 and/or proximal 516 sections of the catheter 508 may be slid or axially adjusted along the pump's rotational axis 518 between axial positions toward and away from the other. With the distal 514 and proximal 516 sections adjusted to a position generally relatively away from each other, portions of the support member 506 may be pulled closer to the pump's rotational axis 518, thereby causing the flexible web 504 to be retracted therewith to a collapsed, deployment configuration. As the distal 514 and proximal 516 sections are adjusted to a position generally relatively toward each other, portions of the support member 506 may be forced away from the pump's rotational axis 518, thereby causing the flexible web 504 to be expanded therewith to an expanded, operable configuration, as illustrated in FIG. 5A. With the flexible web 504 in an expanded, operable configuration, the angle of the flexible web, and thus the impeller blade surface, may be created or modified by rotation of either or both of the distal 514 and/or proximal 516 sections of the catheter 410 with respect to one another, as illustrated in FIG. 5B.

The flexible webs of the various embodiments of cannulas described above may be manufactured from any suitable materials. For example, the various embodiments of cannulas described above may be manufactured from, but are not limited by, a polymer, a metal or metal alloy, a shape memory material, or combinations of materials.

Cannula

In general, the various embodiments of cannulas of the present disclosure may include a plurality of support members or ribs, and may be activated between a collapsed, deployment configuration and an expanded, operable configuration by changing the relative position of the ribs. In some embodiments, as noted above, the cannula may be activated between a collapsed, deployment configuration and an expanded, operable configuration separately from an activation of the impeller between a collapsed, deployment configuration and an expanded, operable configuration. In an expanded, operable configuration, a conduit may be created within which the pump's impeller may be expanded and operated. Operation of the impeller can generate blood flow within the cannula between the cannula's inlet and outlet, which may typically be provided at the proximal and distal ends, respectively, of the cannula. In some embodiments, the cannula may also provide separation between any surrounding tissue and the impeller.

Figure 6:
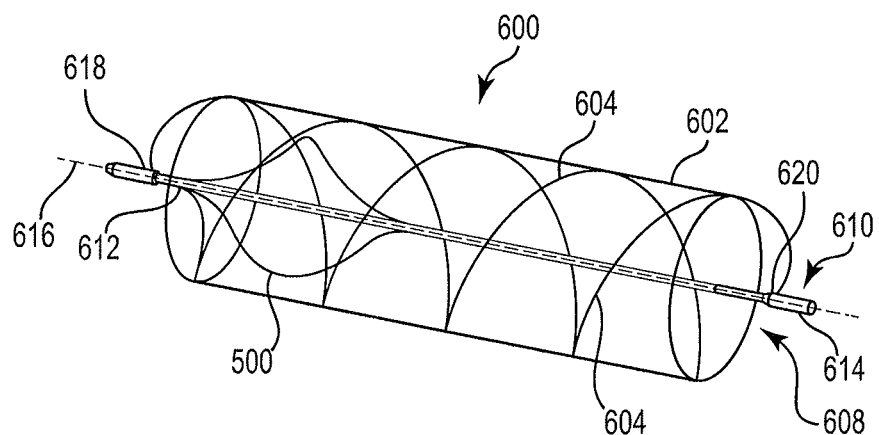
FIG. 6 is a perspective view of a cannula according to one embodiment of the present disclosure.
Figure 7:
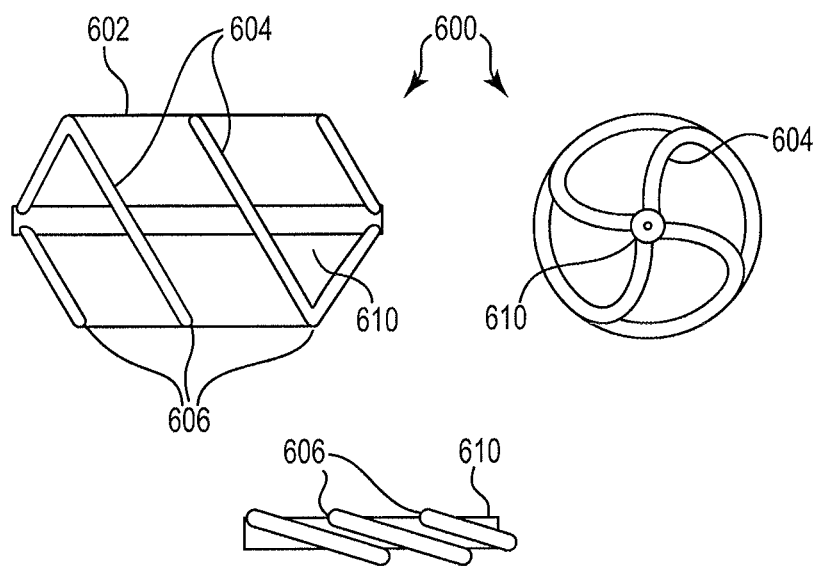
FIG. 7 includes side and end schematic views of the cannula embodiment of FIG. 6 in an expanded configuration and an end schematic view of the cannula embodiment of FIG. 6 in a collapsed configuration.

In one embodiment, illustrated in FIG. 6 and schematically in FIG. 7, a cannula 600 may include a thin, flexible film or mesh cover 602 supported by or between one or more substantially rigid or semi-rigid support members 604 in spiral configuration, creating a plurality of ribs 606. In an expanded, operable configuration, as illustrated in FIG. 6, the ribs 606 may stretch and/or support the cover 602 to create a conduit 608, in which the impeller (e.g., impeller 500 as shown in FIG. 6; although any of the above described impellers are suitable) may by expanded to its operable configuration. In some embodiments, the substantially rigid or semi-rigid support members 604 in spiral configuration may be biased to the expanded, operable configuration.

The cannula 600 may be adjusted to a collapsed, deployment configuration, as illustrated at the bottom of FIG. 7. In one embodiment, with reference again to FIG. 6, the catheter 610 may include a catheter layer having a distal section 612 and a proximal section 614, with either or both sections axially positionable along the pump's rotational axis 616, such that the distal and proximal sections may be axially positioned relative to one another. The cannula 600, or more particularly in some embodiments, the support members 604, may be attached at one end 618 to the distal section 612 and at one end 620 to the proximal section 614, thereby permitting the ends of the cannula 600, or support members 604, to also be axially positioned relative one another by means of the distal and proximal sections. Thus, in one embodiment, the cannula 600 may be adjusted to a collapsed, deployment configuration by causing the support members 604 to be adjusted axially generally relatively away from each other, thereby causing portions of the support members to be pulled closer to the pump's rotational axis 616, and causing the flexible mesh cover 602 to be retracted therewith.

In addition or alternatively, either or both of the distal 612 and proximal 614 sections may be rotatable about the pump's rotational axis 616, such that the distal and proximal sections may be rotated relative to one another. In this regard, the ends of the cannula 600, or support members 604, may additionally or alternatively be rotatably positioned relative one another by means of the distal 612 and proximal 614 sections. Thus, in one embodiment, the cannula 600 may be adjusted to a collapsed, deployment configuration by additionally or alternatively causing the ends of the spiral support members 604 to be rotated relative one another other, thereby shrinking the size of the conduit 608 and collapsing the mesh cover 602 supported therebetween.

However, any other suitable means for permitting distal 618 and proximal 620 ends of the support members 604 to move axially and/or rotatably relative one another are considered within the spirit and scope of the present disclosure. In a further embodiment, cannula 600 and/or catheter 610 may include a drawstring, which may be pulled to gather up any loose material of the retracted mesh cover 602 and hold the mesh cover relatively closer to the catheter body.

Figure 8:
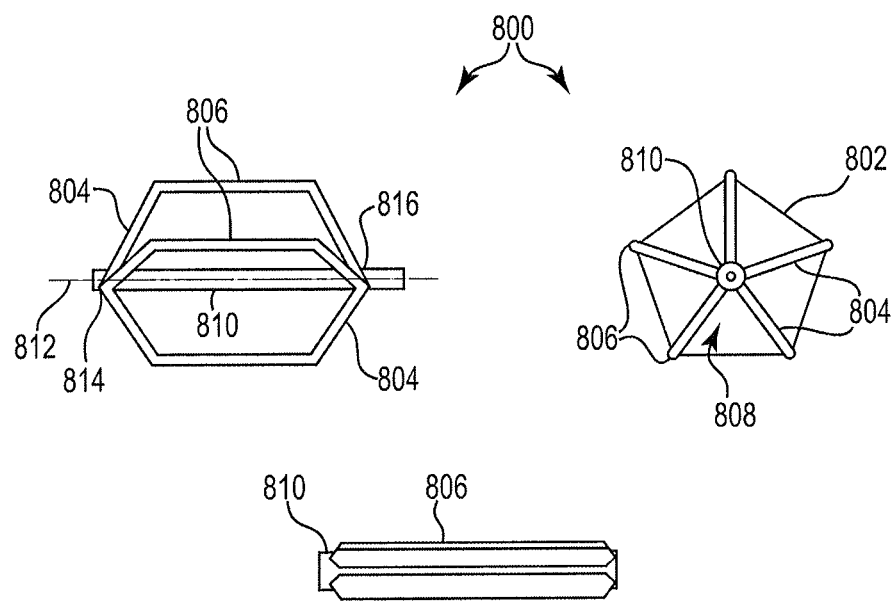
FIG. 8 includes side and end schematic views of a cannula according to another embodiment of the present disclosure in an expanded configuration and an end schematic view of the cannula in a collapsed configuration.

In another embodiment, illustrated schematically in FIG. 8, a cannula 800 may include a thin, flexible film or mesh cover 802 supported by or between one or more substantially rigid or semi-rigid support members 804 in a linear, axial configuration, creating a plurality of ribs 806 that are generally aligned parallel to the catheter body. In an expanded, operable configuration, the ribs 806 may stretch and/or support the cover 802 to create a conduit 808, in which the impeller may by expanded to its operable configuration. In some embodiments, the substantially rigid or semi-rigid support members 804 in a linear, axial configuration may be biased to the expanded, operable configuration.

Similar to the embodiments of FIGS. 6 and 7, the cannula 800 may be adjusted to a collapsed, deployment configuration, as illustrated at the bottom of FIG. 8. In one embodiment, as discussed above, the catheter 810 may include a catheter layer having a distal section and a proximal section, with either or both sections axially positionable along the pump's rotational axis 812, such that the distal and proximal sections may be axially positioned relative to one another. The cannula 800, or more particularly in some embodiments, the support members 804, may be attached at one end 814 to the distal section and at one end 816 to the proximal section, thereby permitting the ends of the cannula 800, or support members 804, to also be axially positioned relative one another by means of the distal and proximal sections. Thus, in one embodiment, the cannula 800 may be adjusted to a collapsed, deployment configuration by causing the support members 804 to be adjusted axially generally relatively away from each other, thereby causing portions of the support members to be pulled closer to the pump's rotational axis 812, and causing the flexible mesh cover 802 to be retracted therewith.

As with the above embodiments, any other suitable means for permitting distal 814 and proximal 816 ends of the support members 804 to move axially relative one another are considered within the spirit and scope of the present disclosure. In a further embodiment, cannula 800 and/or catheter 810 may include a drawstring, which may be pulled to gather up any loose material of the retracted mesh cover 802 and hold the mesh cover relatively closer to the catheter body.

Figure 9:
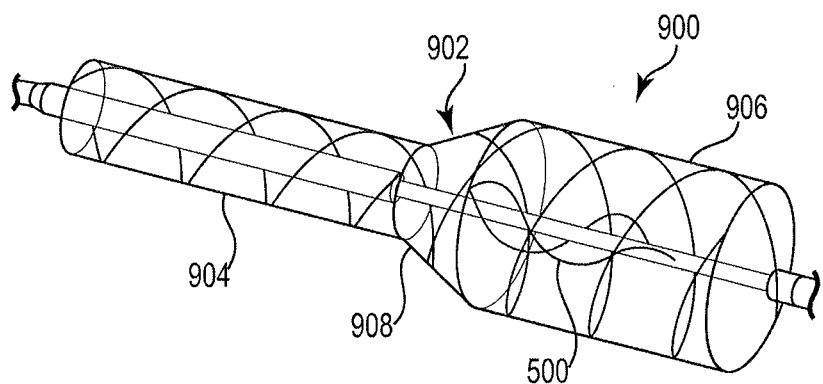
FIG. 9 is a perspective view of a cannula according to still a further embodiment of the present disclosure having various diameters along its axial length.

In some embodiments, as illustrated in FIGS. 6-8, the cannula may have a generally constant diameter axially along the catheter body. However, in other embodiments, as illustrated for example in FIG. 9, the cannula 900 may have a diameter that varies axially along the catheter body 902. In such embodiments, the cannula 900 may have two or more axial sections 904, 906 of substantially constant diameters and one or more axial sections of transition 908 from one section of constant diameter to a different section of constant, but different, diameter. An impeller, such as those described above, may be provided in any suitable axial section. As illustrated, an impeller (e.g., impeller 500 as shown in FIG. 9; although any of the above described impellers are suitable) may be provided within a proximal axial section 906 of relatively larger diameter than a distal axial section 904. In such an embodiment, the transition from a relatively larger diameter conduit to a relatively smaller diameter conduit may also increase the rate of flow through the distal axial section 904 and out of cannula 900.

According to some embodiments, operation of an impeller within the various embodiments of cannulas described herein may cause a flow of fluid, e.g., blood, into an inlet opening at one end of the cannula, through the cannula, and out an outlet opening at an opposite end of the cannula. Generally, the flow of fluid may be substantially axial with the axis of rotation of the impeller. However, in some embodiments, a cannula may additionally, or alternatively include outlet openings that permit the flow of fluid out of the cannula substantially perpendicularly to the axis of rotation of the impeller. In still other embodiments, a cannula may include multiple inlets, and/or multiple outlets, which may assist in preventing blockages of the inflow and/or outflow of fluid to or from the pump.

Figure 10A:
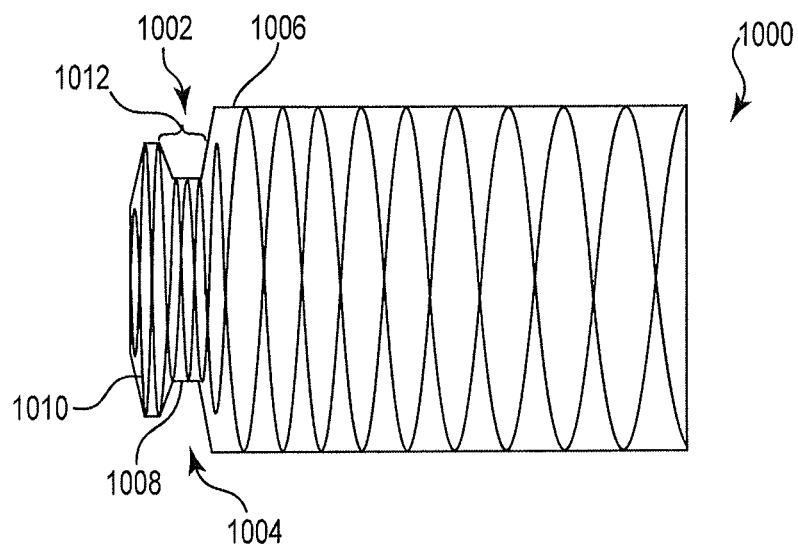
FIG. 10A is a side view of a cannula according to yet another embodiment of the present disclosure having a port fixation feature.
Figure 10B:
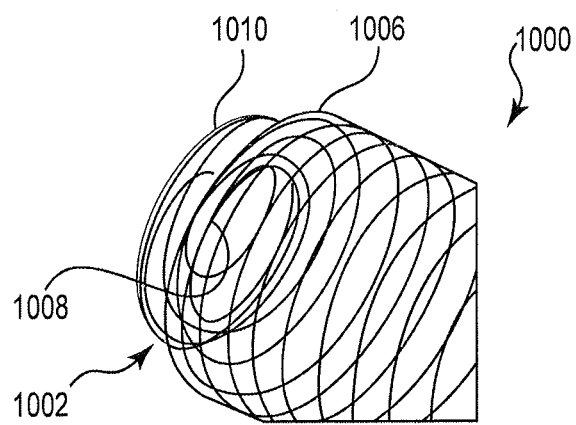
FIG. 10B is a perspective view of the cannula of FIG. 10A.

In still further embodiments, as illustrated in FIGS. 10A and 10B, a cannula 1000 may include one or more features 1002 for port fixation. More specifically, as shown in cross-section in FIG. 11A, where there is an opening 1102 in the wall, for example but not limited to, between any combination of heart chamber(s) and blood vessel(s), the cannula 1000 may be configured such that it can be placed in the opening, expanded as described in various manners above, and remain substantially affixed with respect to the opening by means of the one or more features 1002 for port fixation, as illustrated in cross-section in FIG. 11B. In one particular embodiment, one end of the cannula 1000, such as but not limited to, the distal end 1004, may include an impeller conduit section 1006, a neck section 1008, and a port fixation section 1010. As described with respect to the various cannula embodiments above, the cannula 1000, including the impeller conduit section 1006, neck section 1008, and a port fixation section 1010, may be adjusted between a collapsed, deployment configuration and an expanded, operable configuration. As illustrated in FIGS. 10A and 10B, in the expanded, operable configuration, the neck section 1008 may be configured to expand to a diameter that is smaller than the expanded diameter of the impeller conduit section 1006 and the port fixation section 1010, thereby forming a generally hourglass shape having a pocket 1012 created between the impeller conduit section and the port fixation portion at the neck section. As illustrated in FIG. 11B, the cannula 1000 may be expanded at a position such that the pocket 1012 formed at the neck section 1008 upon expansion of the cannula may generally align with the wall opening 1102. The relatively larger diameters of the impeller conduit section 1006 and the port fixation section 1010 can be designed such that they do not easily pass through the wall opening 1102 when the cannula is in the expanded, operable configuration, and thus cause the cannula 1000 to remain substantially affixed with respect to the opening by means of the pocket 1012. In additional embodiments, as shown in FIG. 11C, an intermediate device 1104, such as a port or similar device, may be fixed at the wall opening 1102 to, for example only, improve the opening strength and/or improve the opening geometry.

The flexible film or mesh covers of the various embodiments of cannulas described above may be manufactured from any suitable materials, such as but not limited to a polymer, a metal or metal alloy, a shape memory material, or combinations of materials. In further embodiments, the various embodiments of cannulas described above may be provided without the flexible film or mesh covers, thereby leaving the support members exposed.

With reference again to FIG. 1, in one embodiment, the various embodiments of impellers and cannulas described in the present disclosure may be adjusted, for example to expand and retract the impellers and/or cannulas between the expanded, operable configuration and collapsed, deployment configuration, using a plurality of concentric layers or sheaths of the catheter, as will be described in further detail below. Generally, however, in one embodiment, the plurality of concentric layers may include, a drive shaft layer, translatable along the catheter's axial direction for adjusting the impeller, and a cannula sheath, translatable along the catheter's axial direction for adjusting the cannula. In alternative or additional embodiments, the drive shaft layer and/or the cannula sheath may be rotatable about the axis of rotation, so as to permit, for example, the variation in impeller blade angle and/or to assist in, for example, collapsing a spiral support member or flexible mesh cover, as described above.

Guidance System

Figure 12:
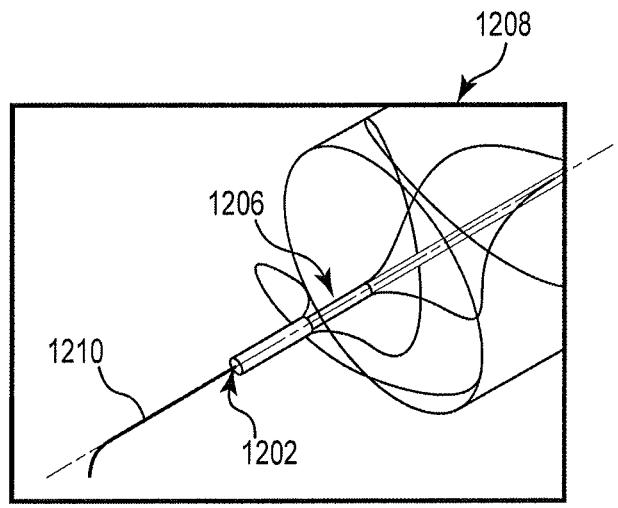
FIG. 12 is a perspective view of a catheter guidance system according to one embodiment of the present disclosure.

In general, the various embodiments of pumps disclosed herein may include a means or guidance system for directing the catheter and pump into and through the vasculature to the desired anatomical position, for example, at the heart. Such means or guidance system, according to one embodiment of the present disclosure, illustrated in FIG. 12, may include an opening or passageway 1202 through the central axis 1204 of the catheter 1206, such that the catheter and pump 1208 may be inserted over and travel along a guidewire 1210 as will be understood by those skilled in the art.

Figure 13:
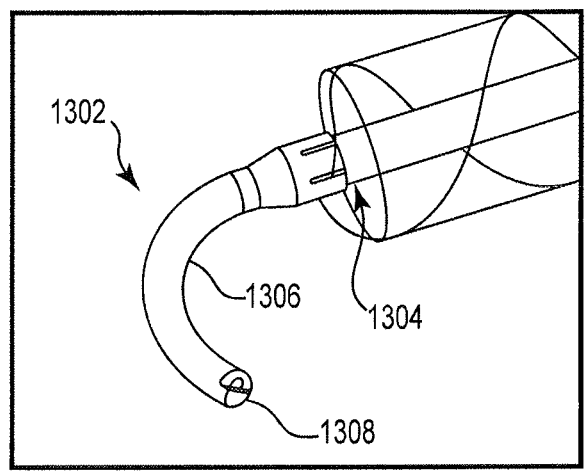
FIG. 13 is a perspective view of a catheter guidance system according to another embodiment of the present disclosure.

In another embodiment, illustrated in FIG. 13, a means or guidance system for directing the catheter and pump into and through the vasculature to the desired anatomical position may include a steerable catheter tip 1302. More specifically, the catheter 1304 may include a generally flexible section 1306 at or near its distal end. The flexible section 1306 may have an adjustable curvature that permits the flexible section of the catheter to be adjusted to aim the catheter in the desired direction of travel. In one embodiment, the flexible section 1306 may have a bias for curvature in a predetermined direction, or in some embodiments may have a bias for no curvature. The flexible section 1306 may include a cable therewithin and anchored thereto for controlling the curvature of the flexible section, the cable running through the catheter to an external control system. In a particular embodiment, the cable is anchored at or near the tip 1308 of the flexible section 1306, which may permit ease of control. The cable may be used to control the flexible section 1306 by, for example, manipulating or pulling the cable at the external control system to cause a desired curvature of the flexible section. Similarly, when the cable is manipulated in a different direction or released, the flexible section 1306 may return to its normal biased position.

Power Transmission System

In general, the various embodiments of pumps disclosed herein may include a means or power transmission system in the catheter for driving the impeller. The transmission system may be controlled, for example, from a control and/or power unit operably connected at or to an external end of the catheter. The power transmission system may generally provide a means of transferring power from the external control and/or power unit to the mechanical power needed by the pump or impeller.

Figure 14:
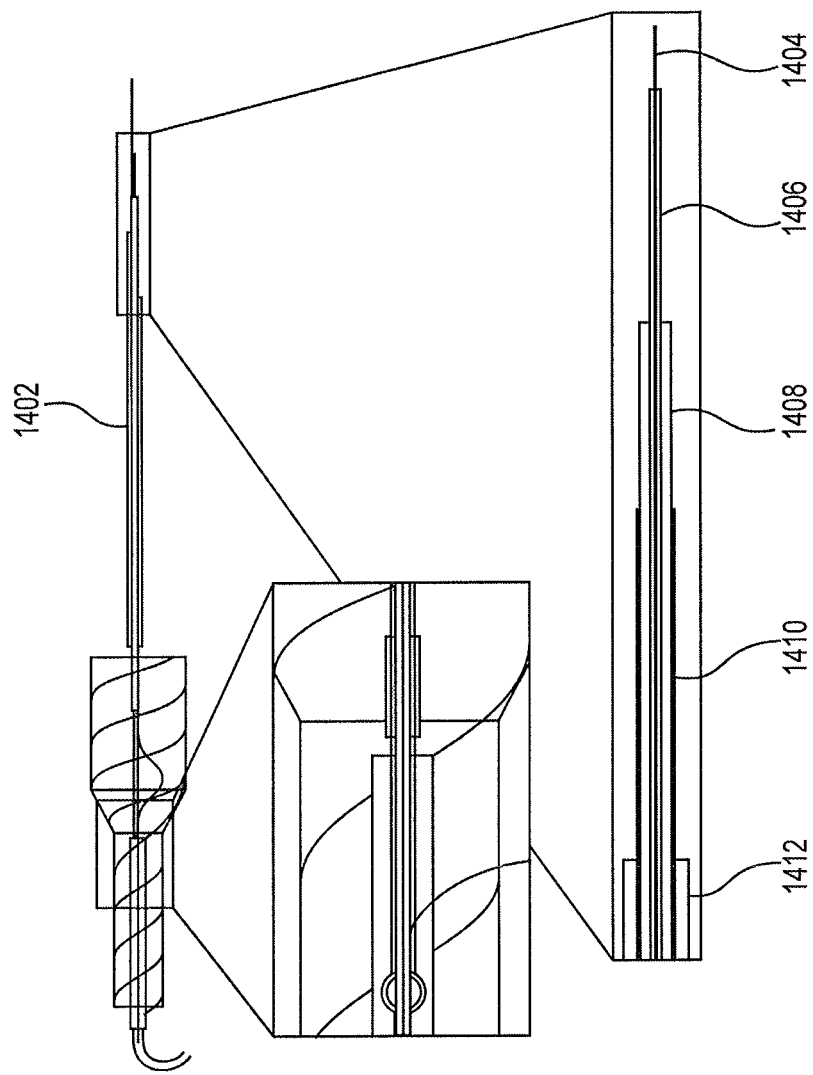
FIG. 14 includes a side view and exploded side views of a power transmission system of a pump according to one embodiment of the present disclosure.

In one embodiment, as illustrated in FIG. 14, the transmission system may include a drive shaft that connects the impeller directly with a drive motor of the control and/or power unit through a clutch. In one embodiment, as described briefly above, the catheter 1402 may include a plurality of concentric layers. In one embodiment, these layers in order of innermost to outermost, may include but are not limited to, a cable 1404, an inner catheter sheath 1406, a rotatable layer 1408 of the drive shaft, a drive shaft layer 1410 that is axially positionable with respect to the rotatable layer 1408 and may, in some embodiments, be rotatable therewith, and an axially positionable cannula sheath 1412. The cable 1404 may be used, for example, to control the guidance system, such as a steerable catheter tip, described above; however, in other embodiments, the cable 1404 may be eliminated leaving a passageway for a guidewire along which the catheter travel may travel, as described above. The inner catheter sheath 1406 may surround the cable 1404. The rotatable drive shaft layer 1408 may provide the rotational motion for the impeller and transfer the rotational motion thereto. The drive shaft layer 1410, which is axially positionable with respect to the rotatable layer 1408, may be used, as described above, to retract and deploy any of the impeller embodiments of the present disclosure. The cannula sheath 1412 may be axially positionable with respect to the inner catheter sheath 1406 and may be used, as described above, to retract and deploy any of the cannula embodiments of the present disclosure.

In one embodiment, the drive shaft layers 1408, 1410 may be longitudinally-flexible, but torsionally rigid, thereby permitting the drive shaft to have flexibility when be maneuvered through the vasculature, but maintaining its ability for delivering rotational motion. One or both of the drive shaft layers 1408, 1410 may be lubricated with a lubricating fluid, such as but not limited to saline. The rotatable drive shaft layer 1408 or both drive shaft layers 1408, 1410, as thus described, may be used to control the pump by delivering or transferring rotational motion to the impeller.

Figure 15:
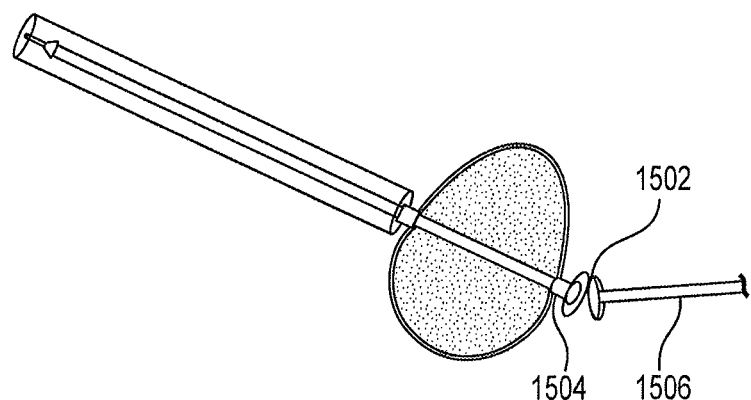
FIG. 15 is a perspective view of a power transmission system of a pump according to another embodiment of the present disclosure.

In a further embodiment, illustrated in FIG. 15, the transmission system may include drive shaft means generally configured as that described above, except that at one or more locations along the drive shaft, a set of gears 1502 may be employed to permit relatively sharper bends or angles in the drive shaft between a distal drive shaft section 1504 and a proximal drive shaft section 1506, while maintaining torque along the drive shaft. In some embodiments, the drive shaft sections 1504, 1506, with gears 1502 at their adjacent ends can be brought into contact with one another or maintain contact with one another via tensioning means, such as but not limited to a cable or sheath. The angle between the drive shaft sections 1504, 1506 may be adjustable.

Figure 16:
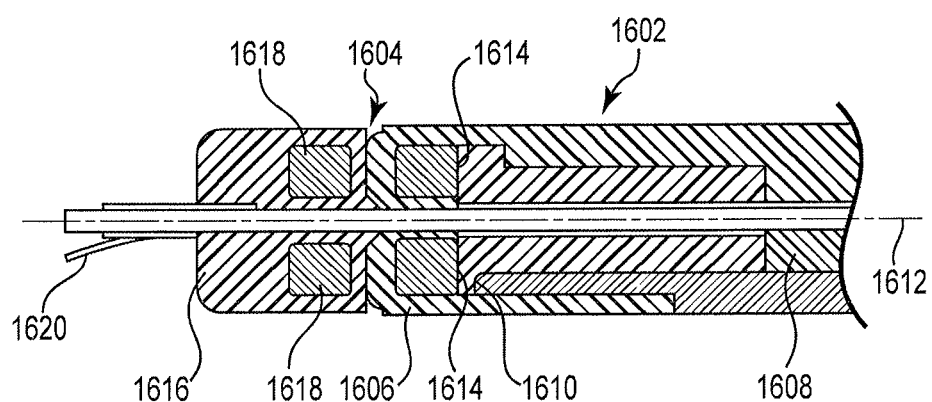
FIG. 16 is a perspective view of a power transmission system of a pump according to still a further embodiment of the present disclosure.

In another embodiment, illustrated in FIG. 16, the transmission system may include a fluid driven or hydrostatic transmission system 1602 in combination with a magnetic coupling device 1604. In general, an external system may drive a fluid to a mechanical generator, causing rotational motion of the mechanical generator, which is transferred to the impeller via a magnetic couple. In a particular embodiment, the hydrostatic transmission system 1602 may include a catheter body or outer sheath 1606 and an inner sheath 1608, concentrically positioned within the outer sheath, the distal ends of which are operably connected with a mechanical generator 1610. The inner sheath 1608 may provide an inlet channel or lumen by which to deliver fluid from the external system to the mechanical generator 1610, while the outer sheath 1606 may provide an outlet channel or lumen by which to return fluid from the mechanical generator to the external system; of course, in other embodiments, the outer sheath may provide the inlet channel while the inner sheath may provide the outlet channel. The mechanical generator 1610 may convert the axial motion of the fluid passing therethrough to rotational motion of the generator about the central axis 1612 of the catheter. At or near a distal end of the generator 1610, the generator may include a proximal end of the magnetic coupling device 1604, including one or more magnets 1614. The magnets 1614 may, by means of the rotational motion of the generator, also rotate therewith about the central axis 1612 of the catheter, creating a changing magnetic field at the distal end of the mechanical generator 1610.

Positioned at or near the distal end of the hydrostatic transmission system 1602 may be the distal end of the magnetic coupling device 1604 having a housing 1616 also including one or more magnets 1618 which interact with the magnets 1614 of the proximal end of the magnetic coupling device to cause rotational motion of housing 1616. More specifically, the changing magnetic field created by the rotational motion of magnets 1614 of the proximal end of the magnetic coupling device 1604 interacts with the magnets 1618 in housing 1616 causing rotational motion thereof.

An impeller 1620, such as any of the various embodiments of impellers described herein, may be operably connected with the distal end of the magnetic coupling device 1604 or housing 1616 and thus rotate therewith. One advantage of such fluid driven or hydrostatic transmission system 1602 in combination with a magnetic coupling device 1604 is impeller interchangeability since the indirect connection provided by the magnetic coupling device between the transmission system and the impeller provides a relatively easy interconnect for changing between impeller embodiments.

Figure 17:
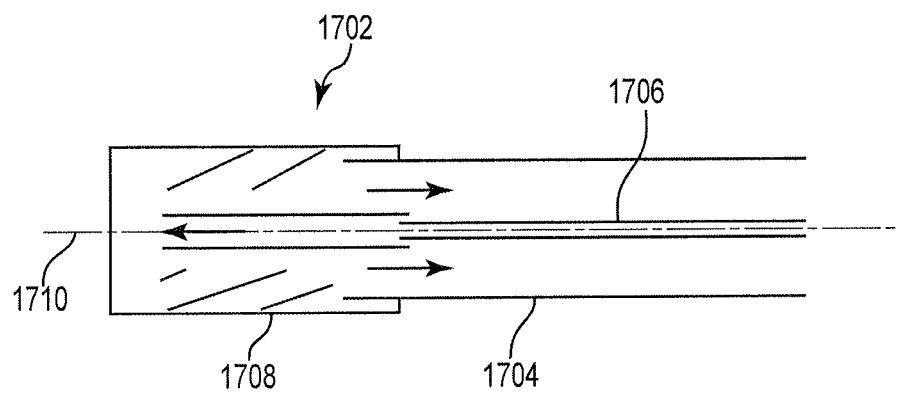
FIG. 17 is a perspective view of a power transmission system of a pump according to yet another embodiment of the present disclosure.

In another embodiment, illustrated schematically in FIG. 17, the transmission system may simply include a fluid driven or hydrostatic transmission system 1702 driving an operably connected impeller. In general, an external system may drive a fluid to a mechanical generator, causing rotational motion of the mechanical generator, which is transferred substantially directly to the impeller. In a particular embodiment, the hydrostatic transmission system 1702 may include a catheter body or outer sheath 1704 and an inner sheath 1706, concentrically positioned within the outer sheath, the distal ends of which are operably connected with a mechanical generator 1708. The inner sheath 1706 may provide an inlet channel or lumen by which to deliver fluid from the external system to the mechanical generator 1708, while the outer sheath 1704 may provide an outlet channel or lumen by which to return fluid from the mechanical generator to the external system; of course, in other embodiments, the outer sheath may provide the inlet channel while the inner sheath may provide the outlet channel. The mechanical generator 1708 may convert the axial motion of the fluid passing therethrough to rotational motion of the generator about the central axis 1710 of the catheter. The mechanical generator 1708 may be directly connected to the impeller, such as any of the various embodiments of impellers described herein; however, it is recognized that any suitable means for indirectly or operably connecting the mechanical generator 1708 and impeller, such as but not limited to a gearing system, are within the spirit and scope of the present disclosure.

With respect to the various fluid driven or hydrostatic transmission systems described above, a fluid driven or hydrostatic transmission system may be externally connected with, for example, a hydraulic connector or compressible tube, which mates the fluid driven or hydrostatic transmission system to an external controller for driving the fluid, as will be understood by those skilled in the art. The external controller may or may not be a component of the control and/or power unit, described herein.

In yet another embodiment, the transmission system may be electrically driven. More specifically, the impeller, such as any of the various embodiments of impellers described herein, may be operably connected with a motor at or near the pump end of the catheter. An electrical system may be driven by the control and/or power unit operably connected at or to an external end of the catheter and may condition the energy for use in controlling the motor and rotating the impeller, as will be recognized by those skilled in the art. The electrical system, or a portion thereof, may be located at or near the motor or may be positioned at any other suitable location, including but not limited to at the control and/or power unit operably connected at or to an external end of the catheter. The electrical system and control and/or power unit may be operably connected by means of electrical connectors or conductors.

Figure 18:
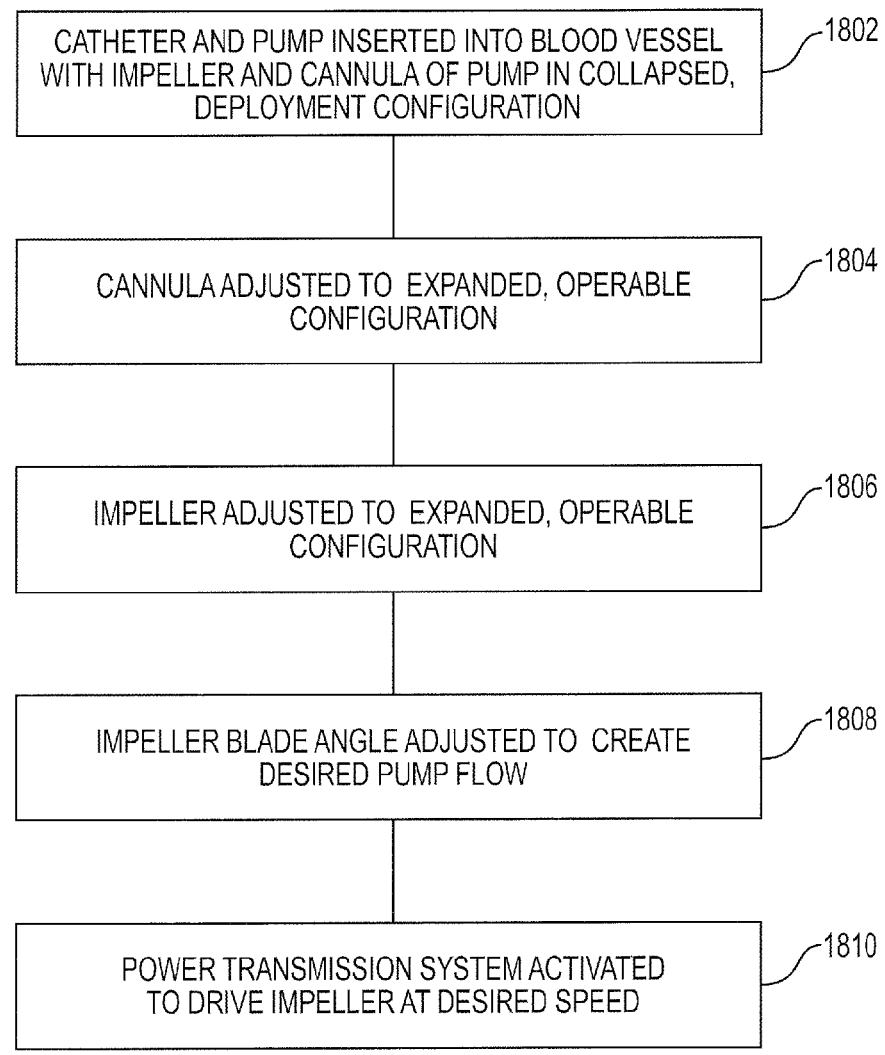
FIG. 18 is a flow diagram of a method of deploying and using and expandable blood pump according to one embodiment of the present disclosure.

A method of deploying and using an expandable blood pump according to the various embodiments described herein is described with reference to FIG. 18. As illustrated at step 1802, a catheter with a pump at or near the distal end thereof may be inserted into a major blood vessel and guided to the desired location, such as at the heart. As described in detail above, the pump may include an impeller and cannula, and the impeller and cannula may be initially inserted in a collapsed, deployment configuration. The impeller and cannula may be biased in the deployment configuration, or alternatively, may be retracted to the deployment configuration using a control unit operably coupled at or near the external end of the catheter. Once the pump is positioned in or near the desired location, e.g., desired chamber of the heart, at step 1804, the clinician or operator may use the control unit to adjust the pump's cannula, as described above, to an expanded, operable configuration, thereby creating a conduit for pump flow. With the cannula expanded and a conduit created, at step 1806, the clinician or operator may adjust the pump's impeller within the cannula into its expanded, operable configuration. Although illustrated as separate steps 1804, 1806, in some embodiments, the adjustment of the cannula and impeller into their expanded, operable configurations may be done substantially simultaneously. At step 1808, if desired, the impeller blade angle may be adjusted, as described in detail above for each of the various impeller embodiments, to create the desired pump flow direction. At step 1810, a power transmission system may be activated, for example using the control unit, to cause rotation of the impeller and generation of pump flow within the cannula between the cannula's inlet(s) and outlet(s). The clinician or operator may enter therapeutic system parameters into the control unit so as to drive the impeller at the desired speed. In general, the collapsed, deployment configuration may permit quick insertion to, and removal from, several anatomical positions while the expanded, operable configuration may permit appropriate therapy.

Although the various embodiments of the present disclosure have been described with reference to preferred embodiments, persons skilled in the art will recognize that changes may be made in form and detail without departing from the spirit and scope of the present disclosure.

The invention claimed is:

1. A pump for inducing flow within a vascular system, the pump comprising:
   a cannula having at least one section adjustable between an operable configuration and a deployment configuration having a substantially smaller diameter than the operable configuration; and
   an impeller positioned within the adjustable section of the cannula and rotatable therein about an impeller axis, the impeller comprising a flexible web suspended by or between one or more moveable support members, the one or more support members being positionable with respect to the cannula between the operable configuration and the deployment configuration by changing a position of the one or more support members, the operable configuration extending at least a portion of the web to a first radial distance from the impeller axis and the deployment configuration collapsing the portion of the web to a second substantially smaller radial distance from the impeller axis.

2. The pump of claim 1, wherein the cannula comprises a spiral support member, the spiral support member spiraling about the impeller axis.

3. The pump of claim 2, wherein the spiral support member is adjustable from the operable configuration to the deployment configuration by twisting.

4. The pump of claim 2, wherein the spiral support member is adjustable from the operable configuration to the deployment configuration by axial positioning proximal and distal ends of the cannula with respect to one another.

5. The pump of claim 1, wherein the cannula comprises a cover supported by a support structure.

6. The pump of claim 5, wherein the cover comprises a plurality of inlet openings for flow into the cannula substantially perpendicular to the impeller axis.

7. The pump of claim 5, wherein the cover comprises an outlet opening for flow to exit the cannula substantially perpendicularly to the impeller axis.

8. The pump of claim 1, wherein the cannula comprises proximal and distal sections having substantially different diameters in the operable configuration.

9. The pump of claim 1, wherein the cannula comprises a port fixation neck between proximal and distal sections.

10. The pump of claim 1, wherein:
    the one or more support members comprises first and second masts supporting the flexible web, the masts in the operable configuration being substantially perpendicular to the impeller axis and in the deployment configuration being substantially parallel to the impeller axis; and
    the pump further comprises a catheter having a distal catheter section supporting the first mast and a proximal catheter section supporting the second mast, the distal and proximal catheter sections rotatable with respect to one other so as to radially offset the first and second masts.

11. The pump of claim 1, further comprising a catheter having proximal and distal portions coupled to proximal and distal ends of the one or more support members, the catheter sections being axially positionable with respect to one another to position the web between the operable and deployment positions.

12. The pump of claim 11, wherein the catheter sections are rotatable with respect to one another so as to radially offset the proximal and distal ends of the support members.

13. The pump of claim 1, further comprising a drive shaft for rotating the impeller, the drive shaft comprising a proximal section having a first gear and a distal section having a second gear for transferring rotational motion to the impeller by adjacent positioning of the first and second gears.

14. The pump of claim 1, further comprising a power transmission system for driving rotational motion of the impeller, the power transmission system comprising:
  a mechanical generator coupled to the impeller for transferring fluid motion into rotational motion about the impeller axis; and
  first and second lumens for driving the fluid motion through the mechanical generator.

15. The pump of claim 1, further comprising a magnetic coupler for rotating the impeller about the axis, the magnetic coupler comprising:
  a first magnet housing rotationally coupled to a mechanical generator; and
  a second magnet housing rotationally coupled to the impeller, the second magnet housing positionable adjacent the first magnet housing to transfer rotational motion from the mechanical generator to the impeller.

16. A method comprising:
  inserting a cannula into a vascular system, the cannula adjustable between an operable configuration and a deployment configuration having a substantially smaller diameter than the operable configuration;
  guiding the cannula to a desired location within the vascular system;
  expanding the cannula from the deployment configuration to the operable configuration;
  expanding an impeller positioned along an axis within the cannula from a collapsed configuration to an expanded configuration by changing a position of one or more support members of the impeller, the impeller having a blade comprising a flexible web suspended by or between the one or more moveable support members, the blade extending to a greater radial distance from the axis in the expanded configuration than in the collapsed configuration.

17. The method of claim 16, further comprising rotating the impeller about the axis to drive fluid through the vascular system.

18. The method of claim 16, further comprising adjusting the impeller to a desired blade angle.

19. The method of claim 16, further comprising collapsing the impeller from the expanded configuration to the collapsed configuration and adjusting the cannula from the operable configuration to the deployment configuration.

20. The method of claim 19, further comprising removing the cannula and the impeller from the vascular system.

* * * * *